United States Patent [19]

Arnauld et al.

[11] Patent Number: 5,741,499
[45] Date of Patent: Apr. 21, 1998

[54] HOMOGENEOUS COMPOSITION COMPRISING FLUORINATED COMPOUNDS AND GLYCOLS, METHOD OF PREPARATION THEREOF AND USE IN COSMETICS

[75] Inventors: Pascal Arnauld, Creteil; Myriam Mellul, L'Hay les Roses, both of France

[73] Assignee: L'Oreal, Paris, France

[21] Appl. No.: 734,673

[22] Filed: Oct. 21, 1996

Related U.S. Application Data

[63] Continuation of Ser. No. 188,336, Jan. 25, 1994, abandoned.

[30] Foreign Application Priority Data

Jan. 25, 1993 [FR] France ................... 93 00912

[51] Int. Cl.$^6$ .................. A61K 7/00; A61K 7/021
[52] U.S. Cl. ............... 424/401; 424/63; 424/64; 514/845; 514/847
[58] Field of Search ................. 424/70.1, 401, 424/70.12, 63, 69; 514/845, 847

[56] References Cited

U.S. PATENT DOCUMENTS

| | | | |
|---|---|---|---|
| 3,972,998 | 8/1976 | Keiner | 424/70 |
| 3,993,745 | 11/1976 | Cella | 424/71 |
| 4,765,975 | 8/1988 | Iovanni | 424/70 |
| 4,895,952 | 1/1990 | Marty | 546/339 |

FOREIGN PATENT DOCUMENTS

| | | |
|---|---|---|
| 0 051 527 | 5/1982 | European Pat. Off. . |
| 0 196 904 | 10/1986 | European Pat. Off. . |
| 0 296 661 | 12/1988 | European Pat. Off. . |
| 0 390 206 | 3/1990 | European Pat. Off. . |
| 0 494 412 | 7/1992 | European Pat. Off. . |
| 0 558 423 | 9/1993 | European Pat. Off. . |
| 2 516 920 | 5/1983 | France . |
| WO 93/11103 | 6/1993 | WIPO . |

*Primary Examiner*—Sally Gardner-Lane
*Attorney, Agent, or Firm*—Jacobson, Price, Holman & Stern, PLLC

[57] ABSTRACT

A homogeneous composition for use in cosmetics and dermatology comprises from 0.1 to 99%, preferably 0.5 to 90% by weight with respect to the total composition weight of at least one organofluorinated hydrocarbon compound or a perfluorinated carbon compound having at least one alcohol, thiol, primary of secondary amine functional group, and from 0.1 to 99%, preferably 0.5 to 70% by weight with respect to the total composition weight of at least one hydrocarbon glycol comprising two hydroxyl radicals.

11 Claims, No Drawings

HOMOGENEOUS COMPOSITION COMPRISING FLUORINATED COMPOUNDS AND GLYCOLS, METHOD OF PREPARATION THEREOF AND USE IN COSMETICS

This application is a continuation of application Ser. No. 08/188,336, filed Jan. 25, 1994, now abandoned.

BACKGROUND OF THE INVENTION

1. Field of the Invention

The present invention concerns compositions comprising a fluorinated hydrocarbon compound or a perfluorinated compound in homogeneous solution with a glycol, a method for preparation thereof and use of these solutions in the cosmetics and dermatological fields.

2. Description of the Prior Art

In cosmetics, prevention of skin ageing is a subject of constant study. One possible way of slowing cutaneous ageing of the skin consists in keeping it well moisturized. Numerous cosmetic and/or makeup compositions aim to accomplish this by associating moisturizing compounds with an appropriate lipophile system to produce a film on the surface of the skin.

This film is intended to limit transepidermal water loss, requiring some hydrophobicity and resistance to secretions such as sweat or sebum, and to external environmental agents. It should also allow the skin to breathe, necessitating permeability to oxygen and carbon dioxide.

Hydrocarbon and silicone oils have already been suggested for use in forming this film as these oils are hydrophobic; however, they have the disadvantage of having low resistance to sebum, resulting in poor staying power of the protective film.

Systems which associate certain hydrophilic substances with fluorinated oils have also been suggested; fluorinated oils have the advantage of an extremely hydrophobic character associated with some lipophobicity. It is, moreover, known, especially in the medical field, that these oils can dissolve gases such as oxygen and carbon dioxide.

Patent document EP-A-196 904 thus describes dispersions of perfluorinated oils in emulsions; however, the insoluble nature of perfluorinated oils, along with a density which is higher than that of the other constituents, results in a non-homogeneous distribution of the oils in the preparations, reducing the performance of the cosmetic products.

Other documents describe emulsification of these fluorinated oils as water-in-oil or oil-in-water systems in the presence of a surfactant. Patent documents EP-A-390 206 and EP-A-494 412 describe emulsions comprising glycerins type polyols and patent document EP-A-296 661 describes emulsions using a fluorinated surfactant.

The stability and cosmetic properties of these systems depend on the presence of the surfactant which is a limiting factor in the cosmetics field.

There is thus the need to develop an alternative to surfactants to produce a compatible association of fluorinated oils and hydrophilic substances without the need for a surfactant system.

SUMMARY OF THE INVENTION

We have now developed homogeneous compositions by associating glycols with fluorinated compounds. The present invention thus concerns homogeneous solutions comprising at least one organofluorinated hydrocarbon compound or perfluorinated compound associated with at least one hydrocarbon glycol.

In the context of the invention organofluorinated hydrocarbon means compounds whose chemical structure comprises a carbon backbone where some hydrogen atoms have been substituted by fluorine atoms, while perfluorinated means compounds wherein the hydrogen atoms bonded to the carbon atoms have been completely substituted by fluorine atoms. The hydrocarbon backbone may comprise one or more heteroatoms and/or one or more functional organic groups.

The substitution ratio for replacement of hydrogen atoms by fluorine atoms is given as follows for organofluorinated hydrocarbon compounds: number of fluorine atoms/(number of fluorine atoms+number of hydrogen atoms) where only those hydrogen atoms bonded to the carbon atoms of the backbone are taken into account. The organofluorinated hydrocarbon compounds or perfluorinated compounds of the invention comprise at least one alcohol, thiol or primary or secondary amine function. The organofluorinated compounds are non volatile, with a boiling point higher than 30° C.

Organofluorinated hydrocarbon compounds or perfluorinated compounds of the invention have the following formula (I):

wherein:

x is 1, 2 or 3, y is 0 or 1 z is 0, 1, 2 or 3, provided that y and z are not simultaneously 0 and that when z is 0 x is 2 or 3, the functional radicals OH, SH, $NH_2$ and HN may indifferently take place on one or more of the radicals $R_F$, A and $R_H$ by insertion (NH) or terminal or pendent substitution (OH, SH, $NH_2$); $R_F$ has at least two of said functional radicals when y and z are both 0. $R_F$ is an a fluorinated saturated or unsaturated aliphatic or aromatic, radical with a linear, branched or cyclic chain which may be functionalized and/or interrupted by divalent atoms such as oxygen or sulfur or trivalent atoms such as nitrogen and/or substituted by hydrogen atoms or other halogen atoms provided that, for any two carbon atoms of the backbone, no more than one of these substituents other than fluorine is present. $R_H$ is a saturated or unsaturated aliphatic or aromatic hydrocarbon, saturated or unsaturated hydrocarbonated radical with a linear, branched or cyclic chain which may be functionalized and/or interrupted by one or more divalent atoms such as oxygen or sulfur or by one or more trivalent atoms such as nitrogen, nitrogen being then fully substituted. A is a di-, tri- or quadrivalent radical such as

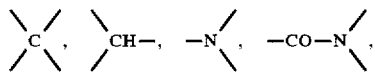

-continued

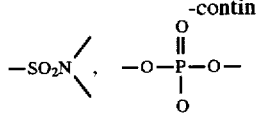

or a cyclic, aliphatic or aromatic group or an unsaturated ethylene group.

In addition to the functional radicals OH, SH, NH$_2$ and NH, R$_F$ and R$_H$ may also comprise other organic functional groups such as an acid, carbonyl, sulfoxide, ester, amide, phosphate, enamine or sulfonomide, said functional groups being inserted or substituted (terminal or pendent).

Unsaturated ethylene structure means, for example:

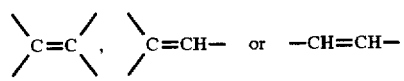

RH is preferably a linear or branched C$_1$–C$_{22}$ alkyl radical or a mixture of linear or branched C$_1$–C$_{22}$ alkyl radicals, a C$_6$–C$_{10}$ aryl radical or a C$_7$–C$_{15}$ aralkyl radical.

R$_F$ is preferably a perfluoroalkyl radical having 4 to 22 carbon atoms.

According to the invention, the substitution ratio for the hydrogen atoms bonded to carbon by fluorine atoms is between 0.5 and 100%, preferably 10 to 100%.

By way of illustration, the organofluorinated hydrocarbon compounds described in patent application PCT/FR-92/01140 having the general structure shown in formula (II) can be mentioned:

$$R_F\text{—}(CH_2)_n\text{—}X\text{—}[C_3H_5(OH)]\text{—}(Y)_x\text{—}R_H \quad (II)$$

wherein

C$_3$H$_5$(OH) is the structure:

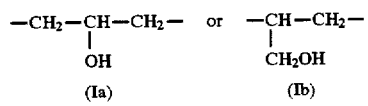

R$_H$ is a linear or branched C$_1$–C$_{22}$ alkyl radical or a mixture of linear or branched C$_1$–C$_{22}$ alkyl radicals or an aryl or aralkyl radical;

R$_F$ is a C$_4$–C$_{22}$ perfluoroalkyl radical;

n is between 0 and 4;

x is O, S

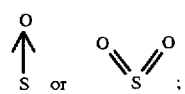

x is 0 or 1;

Y is O, S.

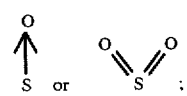

provided that when X is

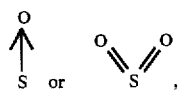

Y is not

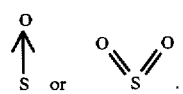

These compounds may be prepared by reacting a fluorinated compound having an acidic hydrogen atom and formula:

$$R_F\text{—}(CH_2)_n\text{—}X\text{—}H$$

with an epoxide having formula:

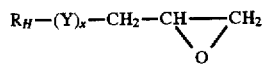

or by reacting a hydrocarbon compound having an acidic hydrogen atom and formula:

$$R_H\text{—}(Y)_x\text{—}H$$

with a fluorinated epoxide having formula:

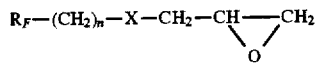

in the presence of a basic or acidic compound acting as reactant or catalyst to obtain the corresponding compound having formula (II), substituents R$_F$, R$_H$, n and x having the meanings given above for formula (II) and X being O or S, Y being O or S, and oxidation if required of the mercaptan moiety to sulfoxide or sulfone with oxygenated water. These compounds are described in WO 93/11103 and EP-A-0 166 696.

Moreover, there may also be used according to the invention the compounds of formula (IV):

$$R_F\text{—}(CH_2)_n\text{—}X\text{—}[C_3H_5(OH)]\text{—}Y\text{—}(CH_2)_m\text{—}R'_F \quad (IV)$$

in which

C$_3$H$_5$(OH) is the structure:

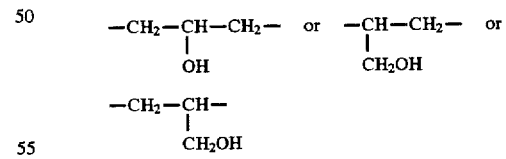

R$_F$ and R'$_F$, which are identical or different, are a linear or branched perfluorinated C$_4$–C$_{20}$ alkyl radical or a mixture of linear or branched perfluorinated C$_4$–C$_{20}$ alkyl radicals;

m and n, which are identical or different, are 0, 1, 2, 3 or 4;

X and Y, which are identical, are —O— or —S—.

These compounds are described in DE-2 702 607, JP 89-193 236, JP 92-275 268 and U.S. Pat. No. 3,893,984.

There may also be used the compounds of formula:

$$R_F\text{—}(CH_2)_n\text{—}X\text{—}[C_3H_5(OH)]\text{—}Y\text{—}(CH_2)_m\text{—}R'_F \quad (I')$$

in which
 $C_3H_5(OH)$ is the structure:

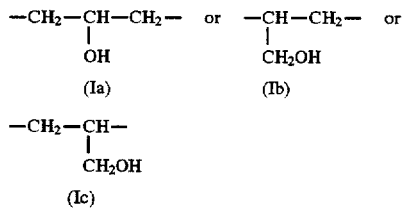

$R_F$ and $R'_F$, which are identical or different, are a linear or branched perfluorinated $C_4$–$C_{20}$ alkyl radical or a mixture of linear or branched perfluorinated $C_4$–$C_{20}$ alkyl radicals;

m and n, which are identical or different, are 0, 1, 2, 3 or 4 and X is O and Y is S or X is S and Y is O.

The compounds of formula (I') can be prepared using the reaction of an acidic hydrogen-containing fluorinated compound of formula (II'):

with an epoxide of formula (III'):

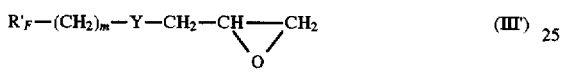

or the reaction of an acidic hydrogen-containing fluorinated compound of formula (IV'):

with a fluorinated epoxide of formula (V'):

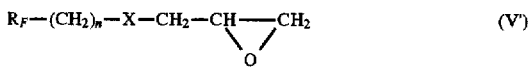

in the presence of a basic or acidic compound playing the part of reagent or catalyst. The compounds are described in FR 9 306 605.

There may also be used, according to the invention, the compounds described in the document DE 2 052 579,of formula:

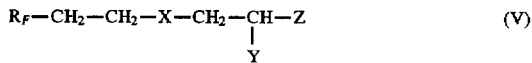

where
Y is OH, and
z is

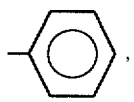

—CH$_3$, —CH$_2$OH, —CH$_2$OCOCH$_3$
or alternatively Y is —CH$_2$OH and Z is —O—COCH$_3$
X is —O—, —S—,

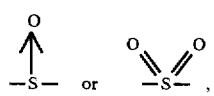

and
$R_F$ is a linear or branched perfluorinated $C_4$–$C_{20}$ alkyl radical or a mixture of linear or branched perfluorinated $C_4$–$C_{20}$ alkyl radicals;

or alternatively the compounds described in the document U.S. Pat. No. 3,952,066, of formula:

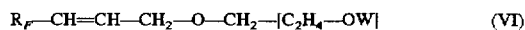

where
$C_2H_4OW$ is:

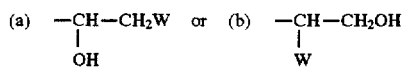

W is:

—OR, —SR, —COOR,

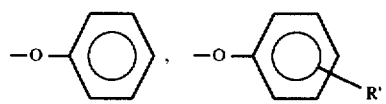

R is a linear or branched $C_1$–$C_{18}$ alkyl radical,

R' is —CH$_3$ or —OH, in the ortho or para position, and $R_F$ is a linear or branched perfluorinated $C_4$–$C_{20}$ alkyl radical or a mixture of linear or branched perfluorinated $C_4$–$C_{20}$ alkyl radicals.

In addition, the products sold by ATOCHEM under the trade name FORALKYL EOH having the formula given below may be mentioned:

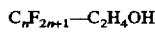

wherein
n is 6 or 8.

Functionalized fluorinated polyethers have formula (III):

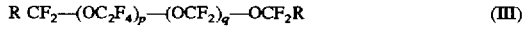

wherein
p/q is from 0.5 to 1.5
and R is CH$_2$OH,
CH$_2$(OCH$_2$CH$_2$)$_t$OH where t is 1 or 2, or
CH$_2$OCH$_2$CHOHCH$_2$OH,
sold by MONTEFLUOS under the respective trade names FOMBLIN ZDOL, FOMBLIN ZDOL TX and FOMBLIN Z TETRAOL.

According to the invention, the fluorinated compound(s) described represent 0.1 to 99% by weight with respect to the total composition weight, preferably 0.5 to 90% by weight.

The solutions of the invention contain one or more polyols comprising two hydroxyl radicals, also termed glycols. The glycols used in accordance with the invention have a hydrocarbon backbone. The hydrocarbon backbone may be aliphatic or aromatic, saturated or unsaturated, with a linear, branched or cyclic chain.

The hydrocarbon glycols may have any molecular weight but they preferably have a chain length of between C$_2$ and C$_{30}$.

Selection of chain length depends on the miscibility and moisturization parameters of the associated fluorinated compound(s).

The two hydroxyl radicals are located independently of each other at any position on the backbone, either pendent or terminally.

The following hydrocarbon glycols may be mentioned, by way of example: ethylene glycol, propylene glycol, diethylene glycol, 1,3-butylene glycol, 3-methyl 1,3-propanediol, isoprene glycol, neopentyl glycol, triethylene glycol, dipropylene glycol, hexylene glycol, 2-ethyl 1,3-hexanediol, 1,2-dihydroxybenzene, resorcinol, cyclohexanedimethanol, styrene glycol, 2-butyl 2-ethyl 1,3-propanediol, 1,2-dodecanediol, polyethylene glycols, polypropylene glycols and polybutylene glycols.

$C_3$–$C_{12}$ hydrocarbon glycol are preferably used.

In accordance with the invention, the glycol(s) represent 0.1 to 99% by weight with respect to the total composition weight, preferably 0.5 to 70% by weight.

Further, when using organofluorinated hydrocarbon compounds having formula (II), the glycols comprise at least four carbon atoms.

In the solution constituted by the fluorinated compound(s) and glycol(s) it is possible, according to the invention, to introduce other compounds customarily used in the cosmetics industry providing that these are homogeneously dissolved or dispersed in the initial solution. They may be either active ingredients or compounds routinely used as excipients.

The additives are added in quantities which are insufficient to result in demixing of the fluorinated compound and the glycol.

The following oils and waxes may be used as additives:

mineral oils such as paraffin oil, vaseline oil and mineral oils with a boiling point of between 310° and 410° C.;

oils of animal origin such as perhydrosqualene;

plant oils such as sweet almond oil, sesame oil, calophyllum oil, palm oil, avocado oil, jojoba oil, olive oil, castor oil, cereal germ oils such as wheatgerm oil;

synthetic esters such as Purcelin oil, butyl myristate, isopropyl myristate, cetyl myristate, isopropyl palminate, butyl stearate, hexadecyl stearate, isopropyl stearate, octyl stearate, isocetyl stearate, decyl oleate, hexyl laurate, propylene glycol dicaparylate, diisopropyl adipate;

fatty alcohols such as oleic alcohol, linoleic alcohol, isostearyl alcohol, octyl dodecanol;

esters derived from lanolic acid such as isopropyl lanolate, isocetyl lanolate;

acetylglycerides, octanoates and decanoates of alcohols and polyalcohols such as those of glycol and glycerol, ricinoleates of alcohols and polyalcohols such as those of cetyl;

mineral waxes such as microcrystalline waxes, paraffin, vaseline, ceresine;

fossil waxes such as ozokerite, montan wax;

animal waxes such as beeswax, spermaceti, lanoline wax, lanoline derivatives such as lanoline alcohols, hydrogenated lanoline, hydroxylated lanoline, acetylated lanoline, fatty acids of lanoline, acetylated lanoline alcohol;

waxes of plant origin such as candellila wax, carnauba wax, Japan wax, cocoa butter;

synthetic waxes such as polyethylene waxes;

hydrogenated oils which are solids at 25° C., such as hydrogenated castor oil, hydrogenated palm oil, hydrogenated tallow, hydrogenated coconut oil;

fatty esters which are solids at 25° C. such as propylene glycol monomyristate, myristyl myristate;

the following waxes may also be mentioned: cetyl alcohol, stearyl alcohol, mono-, di and triglycerides which are solids at 25° C., stearic monoethanolamide, colophony, and its derivatives such as abietates of glycol and glycerol, sucroglycerides and oleates, myristates, lanolates, stearates and dihydroxystearates of calcium, magnesium, zinc and aluminum.

The following silicone compounds may also be mentioned: cyclic dimethylpolysiloxanes, low or high viscosity dimethylpolysiloxanes, silicone gums, organopolysiloxanes such as phenylmethylpolysiloxanes and phenyltrimethylsiloxypolysiloxanes, alkylmethylpolysiloxanes, alkoxymethylpolysiloxanes, silicones including functional groups such as alcohol, amine or thiol moieties.

In addition, the following perfluorinated oils may be mentioned:

oils belonging to the perfluoroalkane group, perfluorocycloalkanes, perfluoropolycycloalkanes, and perfluoro(alkylcycloalkanes), also those belonging to the aromatic perfluorinated hydrocarbon group or those belonging to the perfluorinated hydrocarbon group containing at least one heteroatom, such as tertiary amines, saturated heterocyclic compounds or perfluoropolyethers.

Gelling agents for oily media may also be incorporated, such as for example:

metallic esters such as polyoxyaluminum stearate or aluminum and magnesium hydroxystearate, esters of fatty acids and glycol and triglycerides, mixtures of fatty alcohols, cholesterol derivatives, in particular hydroxycholesterol, argillaceous minerals which swell in oils, belonging to the montmorillonite group.

The solution may also contain filters, vitamins, hormones, antioxidants, preservatives, dyes, perfumes and any lipophilic additive normally used in cosmetics.

In accordance with the invention, the composition may further contain hydrophilic additives such as:

water, polyols with a functionality greater than 2, such as:
glycerol and polyglycerols, 1,2,6-hexanetriol, D-panthenol, sorbitol, mannitol, xylitol, maltitol, glucose, fructose, sucrose and saccharose;

hydrophilic ingredients such as urea, lactic acid;

monoalcohols such as ethanol or isopropanol;

aqueous medium gelling agents such as:
polysaccharides such as cellulose derivatives (carboxymethylcellulose, hydroxypropylmethylcellulose, etc) and xanthane or carob gum, proteins such as keratin, sulfonic keratin, collagen or elastin, silicates such as aluminum and magnesium silicate, acrylic derivatives such as carbomers, glycerol polyacrylates and polymethacrylates, polyethylene glycols, ingredients such as sodium hyaluronate, the sodium salt of pyroglutamic acid, magnesium gluconate, oligoelements and biological derivatives, salts such as magnesium sulfate or sodium chloride, argillaceous minerals which swell in aqueous media such as saponite, hectorite or smectite, amino acids, and dyes.

Solutions in accordance with the invention may also contain powders. The following natural or synthetic powders may be mentioned by way of example: powders of plant origin such as corn, wheat or rice starch, mineral powders such as talc, kaolin, mica, silica, silicates, alumina, zeolites, hydroxyapatite, sericite, titanium dioxide, mica titaniums, zinc oxide, barium sulfate, iron oxides, manganese violet, chromium oxide, ultramarine blue and bismuth oxychloride or boron nitride, metallic powders such as aluminum powder, organic powders such as nylon powders, polyamide powders, polyester powders, cellulose powders, polyethylene powders, polypropylene powders, polystyrene powders and polytetrafluorethylene powders, and organometallic pigments which associate zirconium, barium or aluminum with organic dyes.

These powders which can be used in compositions of the invention may if required be coated with metal salts of fatty acids, amino acids, lecithin, collagen, polyethylene, silicone compounds, fluorinated compounds, fluorosilicone compounds or any other customary coating.

The present invention also concerns a method of preparing the compositions of the invention. The fluorinated compound is mixed with the glycol at a temperature termed the "miscibility temperature" in order to produce a single homogeneous phase which is stable at room temperature.

In some cases mixing may be effected at room temperature. This is particularly the case when all the constituents are liquid or one can dissolve the others.

For reasons of homogeneity, however, heating is sometimes preferable when one or more of the constituents is in the solid or waxy state at room temperature or if dissolution is too slow.

The solutions thus obtained may be in different states at room temperature, i.e. they may be in a liquid, paste or solid form. The physical state depends on the nature of the constituents present.

Additives, when present, are dissolved or dispersed homogeneously at different stages of preparation.

They may be dissolved or dispersed in the solution constituted by the fluorinated compound(s) and the glycol(s) or in each constituent before mixing to produce the solution, either at room temperature or after the solution or constituent is heated.

These solutions have very good sensorial properties due to the coexistence of fluorinated compounds with glycols in the same phase. Compositions containing these solutions are very comfortable, easy to apply and have a very smooth texture.

A particularly soft, protective film having good staying power and permitting good hydration is left after application.

Because of these properties and the wide range of compositions which can be produced according to the invention, these solutions may be used in a wide variety of applications in the cosmetic or dermatological fields.

These solutions in accordance with the invention may be in the form of skin or hair lotions, lipsticks, foundations, eyeshadows, mascaras, cream rouges or eyeliners.

The solutions of the invention or cosmetic compositions prepared from these solutions may also be used in the treatment or care of skin, hair and eyelashes.

DETAILED DESCRIPTION OF THE INVENTION

Further features and advantages of the invention will become apparent from the following description.

EXAMPLES 1 to 28

Solutions were prepared from the following hydrocarbon glycols:

Isoprene glycol: $(CH_3)_2CHOH-CH_2-CH_2OH$;

Hexylene glycol: $(CH_3)_2CHOH-CH_2-CHOH-CH_3$.

The following fluorinated compounds were tested for their ability to dissolve the above glycols:

A: $C_6F_{13}CH=CH_2$ (FORALKYL E6 from ATOCHEM)

B: $C_8F_{17}CH_2CH_2OC(O)-(CH_2)_7-CH=CH-(CH_2)_7-CH_3$, (NO FABLE FO 9982 from NIPPON OILS)

C: $C_6F_{13}CH_2CH_2OH$ (FORALKYL EOH 6 from ATOCHEM)

D: $C_6F_{13}C_2H_4-S-CH_2-CHOH-CH_2OCH_2-CH\text{-}nC_4H_9$
   $\phantom{C_6F_{13}C_2H_4-S-CH_2-CHOH-CH_2OCH_2-CH\text{-}}C_2H_5$ E: $C_6F_{13}-C_2H_4OCH_2-CHOH-CH_2-OCH_2-CH\text{-}nC_4H_9$
   $\phantom{C_6F_{13}-C_2H_4OCH_2-CHOH-CH_2-OCH_2-CH\text{-}}C_2H_5$ F: $C_8F_{17}-C_2H_4S-CH_2-CHOH-CH_2OCH_2-CH\text{-}nC_4H_9$
   $\phantom{C_8F_{17}-C_2H_4S-CH_2-CHOH-CH_2OCH_2-CH\text{-}}C_2H_5$

G: $C_6F_{13}-C_2H_4-S-CH_2-CHOH-C_8H_{17}$

H: $C_8F_{17}-C_2H_4-S-CH_2-CHOH-CH_2O\text{-}n\ C_4H_9$

I: $HOCH_2-(OC_2F_4)_p-(OCF_2)_q-CH_2OH$ (FOMBLIN Z DOL from MONTEFLUOS, molecular weight 2 000)

J: $HO(CH_2CH_2O)_r-CH_2-(OC_2F_4)_p-(OCF_2)_q-CH_2-(OCH_2CH_2)_sOH$ (FOMBLIN Z DOL-TX from MONTEFLUOS, molecular weight 2 200)

K: $HOCH_2CH(OH)-CH_2OCH_2-(OC_2F_4)_p-(OCF_2)_q-CH_2OCH_2-CH(OH)-CH_2OH$ (FOMBLIN Z TETROL from MONTEFLUOS, molecular weight 1 900)

L: $C_8H_{17}-C_2H_4-NH_2$

M: compound from preparation example VI.

N: compound from preparation example VII.

| Example | Fluorinated compound | Isoprene glycol | Hexylene glycol |
|---|---|---|---|
| 1 and 2 | A | 0 | 0 |
| 3 and 4 | B | 0 | 3% |
| 5 and 6 | C | ∞ | ∞ |
| 7 and 8 | D | 15% | ∞ |
| 9 and 10 | E | 17% | ∞ |
| 11 and 12 | F | 7.5% | ∞ |
| 13 and 14 | G | 17% | ∞ |
| 15 and 16 | H | 16% | ∞ |
| 17 and 18 | I | 9% | 8% |
| 19 and 20 | J | 8% | 18% |
| 21 and 22 | K | 16% | 16% |
| 23 and 24 | L | ∞ | ∞ |
| 25 and 26 | M | 8% | ∞ |
| 27 and 28 | N | 8% | ∞ |

The symbol ∞ indicates miscibility in all proportions.

11

The percentage corresponds to the maximum mass ratio of glycol which can be dissolved in the fluorinated compound under consideration.

Solubilities were measured at 25° C. using an optical microscope to view the number of phases.

Examples 1 to 4 are comparative examples.

EXAMPLE 29

3.3 g of hexylene glycol was mixed with 3.4 g of fluorinated compound D and 3.3 g of octylmethoxycinnamate, sold by GIVAUDAN-RAURE under the trade name PARSOL MCX.

Following homogenization, a clear solution constituted by a single phase was obtained. This solution can be used as a sunscreen lotion.

EXAMPLE 30

6 g of compound D was mixed with 2 g of hexylene glycol and 2 g of pheyltrimethicone, sold by DOW CORNING under the trade name DC 556 Fluid.

Following homogenization, a clear solution constituted by a single phase was obtained.

EXAMPLE 31

6 g of compound D was mixed with 2 g of hexylene glycol and 2 g of perfluorodecaline, sold by RHONE-POULENC under the trade name FLUTEC PP5.

Following homogenization, a clear solution constituted by a single phase was obtained.

EXAMPLE 32

6 g of hexylene glycol was mixed with 2 g of fluorinated compound D and 2 g of glycerol.

Following homogenization, a clear solution constituted by a single phase was obtained. This solution can be used as a moisturizing lotion.

EXAMPLE 33

8 g of hexylene glycol was mixed with 1 g of water and 1 g of fluorinated compound D.

Following homogenization, a clear solution constituted by a single phase was obtained. This solution can be used as a moisturizing lotion.

EXAMPLE 34

A solution of 5 g of urea in 5 g of water was prepared.

Following dissolution, 1 g of this solution was taken and mixed with 8 g of hexylene glycol and 1 g of fluorinated compound D.

Following homogenization, a clear solution constituted by a single phase was obtained which can be used as a moisturizing lotion..

EXAMPLE 35

2 g of hexylene glycol was mixed with 8 g of F-hexylethanethiol.

Following homogenization, a clear solution constituted by a single phase was obtained.

EXAMPLE 36

Makeup Removal Lotion

| | | |
|---|---|---|
| A | 1-(2'-F-hexylethylthio)-3-(2"-ethyl-hexyloxy)-2-propanol (Compound D) | 30 g |
| B | Hexylene glycol | 60 g |
| C | (Water | 9.8 g |
| | (Sodium chloride | 0.1 g |
| | (Methylparaben | 0.1 g |

Method

The constituents of phase C were weighed together and heated to 80°C. to dissolve them completely.

Following cooling to room temperature, the hexylene glycol and fluorinated compound were added.

Following homogenization, a lotion constituted by a single clear phase was obtained which can be used as a makeup remover and which left after application a very soft feel due to the presence of the fluorinated oil.

EXAMPLE 37

Lipstick

| | | |
|---|---|---|
| A | (Carnauba wax | 10 g |
| | (Beeswax | 12 g |
| | (Lanoline | 10 g |
| | (1-(2'-F-hexylethylthio)-3-(2"-ethyl-hexyloxy)-2-propanol (Compound D) | 46.40 g |
| B | Hexylene glycol | 10 g |
| | (FD and C Yellow 6 | 7.30 g |
| | (DC Red 7 | 2 g |
| C | (Iron oxide | 1.50 g |
| | (Titanium dioxide | 0.80 g |

Method

The constituents of phase A were weighed together and heated to 90° C. to produce a clear liquid. Phase C was then added.

After reducing the temperature to 80° C., phase B was added.

Following homogenization, the paste was cast into moulds at 80° C.

The lipstick thus obtained was easy to apply, very soft and had moisturizing properties.

EXAMPLE 38

Eyeshadow

| | | |
|---|---|---|
| 1-(2'-F-hexylethylthio)-3-(2"-ethyl-hexyloxy)-2-propanol | | 5.85 g |
| Isoprene glycol | | 0.65 g |
| Iron oxides | | 9.10 g |
| Chromium oxides | | 5.40 g |
| Titanium dioxide | | 2 g |
| Mica | | 22 g |
| Powdered nylon | | 20 g |
| Talc | qsp | 100 g |

PREPARATION EXAMPLES

EXAMPLE I 1-(2'-F-hexylethythio)-3-(2"-ethylhexyloxy)-2-propanol 3.6 g of a methanolic solution of sodium methylate (about 30% −5.54 meq $g^{-1}$) was added over one minute to 152 g of 2-F-hexylethanethiol at a temperature of 25° C., with stirring and in a current of nitrogen.

The mixture was heated to 70° C. The methanol present in the mixture was vacuum evaporated.

2-ethylhexylglycidyl ether (74.4 g) was then added dropwise over one hour. The mixture temperature was maintained between 60° and 70° C. during addition of the epoxide.

The temperature was reduced to 25° C. following addition.

The mixture was neutralized using 20 ml of normal HCl.

1-(2'-F-hexylethylthio)-3-(2"-ethylhexyloxy)-2-propanol was separated by distillation:

BPt=141° C./66.5 Pa.

175 g (77%) of a colorless translucent oil was obtained.
Elementary Analysis

|  | % C | % H | % S | % F |
|---|---|---|---|---|
| Calculated | 40.28 | 4.80 | 5.66 | 43.60 |
| Measured | 40.37 | 4.82 | 5.55 | 43.74 |

EXAMPLE. II 1-(2'-F-octylethylthio)-3-(2"-ethylhexyloxy)-2-propanol

The compound was prepared in analogous fashion to that of example I using:

288 g of 2-F -octylethanethiol 5.4 g of a methanolic solution of sodium methylate (5.54 meq g$^{-1}$)

111.6 g of 2-ethylhexylglycidylether 30 ml of normal HCl 337 g (81%) of a translucent colorless oil was obtained.
Elementary Analysis

|  | % C | % H | % S | % F |
|---|---|---|---|---|
| Calculated | 37.84 | 4.08 | 4.81 | 48.46 |
| Measured | 37.83 | 4.06 | 4.20 | 47.45 |

EXAMPLE III 1-(2'-F-octylethylthio)-3-butyloxy-2-propanol

Following the method described in example I, 40 g (0.31 mole) of butyl and glycidyl ether was condensed with 147.7 g (0.31 mole) of 2-F-octylethanethiol over one hour in the presence of 2.75 g of a methanolic solution of sodium methylate (5.54 meq g$^{-1}$). Following reaction, the mixture was neutralized with 15.5 ml of normal HCl.

Following distillation (138°–142° C./6.65 Pa), 153 g of 1-(2'-F-octylethylthio)-3-butyloxy-2-propanol was obtained in the form of a colorless oil.

Yield=80%.
Elementary Analysis

|  | % C | % H | % S | % F |
|---|---|---|---|---|
| Calculated | 33.45 | 3.14 | 5.25 | 52.92 |
| Measured | 33.52 | 3.23 | 5.14 | 52.67 |

EXAMPLE IV 1-(2'-F-hexylethylthio)-2-decanol

Using the example described in example 1, 78 g (0.5 mole) of 1,2-epoxydecane was condensed with 130 g (0.5 mole) of 2-F-hexylethanethiol over 90 minutes in the presence of 4.4 g of a methanolic solution of sodium methylate (5.65 meq g$^{-1}$).

Following reaction, the mixture was neutralized with 25 ml of normal HCl.

Following distillation (165°–170° C./66.5 Pa), 216 g of a white amorphous solid was obtained which was 1-(2'-F-hexylethylthio)-2-decanol.

Yield=81%.

Melting point=47° C.
Elementary Analysis

|  | % C | % H | % S | % F |
|---|---|---|---|---|
| Calculated | 40.30 | 4.70 | 5.98 | 46.04 |
| Measured | 40.06 | 4.62 | 6.13 | 45.63 |

EXAMPLE V 1-(2'-F-hexylethyloxy)-3-(2"-ethylhexyloxy)-2-propanol 546 g (1.5 mole) of 2-F-hexylethanol was introduced into a 1 liter reactor.

5.61 g of potassium tertiobutylate was added at 25° C. in a nitrogen atmosphere. The mixture was stirred at 25° C. for 30 minutes to dissolve the tertiobutylate in the 2-F-hexylethanol.

The mixture was heated to 150° C. and 93 g (0.5 mole) of 2-ethylhexyglycidylether was added over 75 minutes.

After 24 hours of reaction at 150° C., 5.61 g of potassium burylate was added. The operation was repeated twice at intervals of 24 hours.

The excess 2-F-hexylethanol was evaporated off and on distillation 68 g (20% of 1-(2'-F-hexylethyloxy)-3-(2"-ethylhexyloxy)-2-propanol was obtained.

Boiling point=145° C. at 13.3 Pa.
Elementary Analysis

|  | % C | % H | % F |
|---|---|---|---|
| Calculated | 41.46 | 4.94 | 44.87 |
| Measured | 41.55 | 4.99 | 45.01 |

EXAMPLE VI 1-(2'-F-hexylethylthio)-3-(2"-F-hexylethoxy)-2-propanol 1.33 g of a methanolic solution of sodium methylate (about 30%—5.65 meq g$^{-1}$) was added over one minute to 57 g of 2-F-hexylethanethiol at a temperature of 25° C., with stirring and in a current of nitrogen.

The mixture was heated to 70° C. The methanol present in the mixture was vacuum evaporated.

2-F-hexylethylglycidyl ether (63 g—0.15 mole) was then added dropwise over one hour. The mixture temperature was maintained between 60° and 70° C. during addition of the epoxide.

The temperature was reduced to 25° C. following addition.

The mixture was neutralized using 7.5 ml of normal HCl.

1-(2'-F-hexylethylthio)-3-(2'-F-hexylethoxy)-2-propanol was separated by distillation:

BPt=170° C./133 Pa.

85 g (71%) of a colorless translucent oil was obtained.
Elementary Analysis

|  | % C | % H | % S | % F |
|---|---|---|---|---|
| Calculated | 28.51 | 1.76 | 4.01 | 61.72 |
| Measured | 28.60 | 1.79 | 4.32 | 61.54 |

EXAMPLE VII 1-(2'-F-hexylethlthio)-3-octylthio-2-propanol 0.61 g of a methanolic solution of sodium methylate (about 30%—5.65 meq g$^{-1}$) was added to 10.05 g (0.069 mole) of octanethiol at a temperature of 25° C. in a current of nitrogen.

The mixture was heated to 70° C. The methanol present in the mixture was vacuum evaporated.

2-F-hexylethylthioglycidyl ether (30 g—0.069 mole) was then added dropwise over 30 minutes. The mixture temperature was maintained between 60° and 70° C. during addition of the epoxide.

The temperature was reduced to 25° C. following addition.

The mixture was neutralized using 3.5 ml of normal HCl.

1-(2'-F-hexylethylthio)-3-octylthio-2-propanol was separated by distillation: BPt=178° C./66.5 Pa.

30 g (75%) of a colorless translucent oil was obtained.
Elementary Analysis

|  | % C | % H | % S | % F |
|---|---|---|---|---|
| Calculated | 39.18 | 4.67 | 11.01 | 42.40 |
| Measured | 39.16 | 4.65 | 10.57 | 42.46 |

There is claimed:

1. A homogeneous cosmetic composition consisting essentially of:

0.1 to 99% by weight with respect to the total composition weight of at least one organofluorinated hydrocarbon compound or a perfluorinated carbon compound having the following formula (I):

$$(R_F)_x\text{—}(A)_y\text{—}(R_H)_z \qquad (I)$$

wherein:

x is 1, 2 or 3, y is 0 or 1, z is 0, 1, 2 or 3, provided that y and z are not simultaneously 0 and that when z is 0, x is 2 or 3, the functional radicals OH, SH, NH$_2$ and NH may be on one or more of the radicals R$_F$, A and R$_H$ by insertion in the case of NH or terminal or pendent substitution in the case of OH, SH and/or NH$_2$; R$_F$ has at least two of said functional radicals when y and z are both 0, R$_F$ is an aliphatic or aromatic, saturated or unsaturated, fluorinated radical with a linear, branched or cyclic chain which may be functionalized and/or interrupted by oxygen or sulfur or nitrogen and/or substituted by hydrogen atoms or other halogen atoms provided that, for any two carbon atoms of the backbone, no more than one of these substituents other than fluorine is present.

R$_H$ is an aliphatic or aromatic, saturated or unsaturated, hydrocarbon radical with a linear, branched or cyclic chain which may be functionalized and/or interrupted by one or more oxygen or sulfur atoms or by one or more nitrogen atoms.

A is a di-, tri- or quadrivalent radical which is $$\diagup\hspace{-0.3em}\diagdown\hspace{-0.6em}\text{C}\hspace{-0.6em}\diagup\hspace{-0.3em}\diagdown\;,\quad \diagdown\hspace{-0.6em}\text{CH—}\hspace{-0.3em}\diagup\;,\quad -\text{N}\hspace{-0.6em}\diagup\hspace{-0.3em}\diagdown\;,\quad -\text{CO—N}\hspace{-0.6em}\diagup\hspace{-0.3em}\diagdown\;,$$

$$-\text{SO}_2\text{N}\hspace{-0.6em}\diagup\hspace{-0.3em}\diagdown\;,\quad -\text{O}-\overset{\overset{\displaystyle O}{\|}}{\underset{\underset{\displaystyle O}{|}}{\text{P}}}-\text{O}-$$

or unsaturated ethylene;

or A is

—(CH$_2$)$_n$—X—[C$_3$H$_5$(OH)]—(Y)'$_x$— wherein

C$_3$H$_5$(OH) is the structure:

—CH$_2$—CH—CH$_2$—   or   —CH—CH$_2$—
        |                              |
        OH                          CH$_2$OH
    (Ia)                              (Ib)

n is between 0 and 4;

X is O, S, $$\overset{\displaystyle O}{\underset{\displaystyle S}{\uparrow}}\quad \text{or}\quad \overset{O\diagdown\hspace{-0.4em}\diagup O}{\underset{\displaystyle S}{\text{\hspace{0.3em}}}}\;;$$

x is 0, or 1;

Y is O, S $$\overset{\displaystyle O}{\underset{\displaystyle S}{\uparrow}}\quad \text{or}\quad \overset{O\diagdown\hspace{-0.4em}\diagup O}{\underset{\displaystyle S}{\text{\hspace{0.3em}}}}\;;$$

provided that when X is
Y is not $$\overset{\displaystyle O}{\underset{\displaystyle S}{\uparrow}}\quad \text{or}\quad \overset{O\diagdown\hspace{-0.4em}\diagup O}{\underset{\displaystyle S}{\text{\hspace{0.3em}}}}$$

or A is

—(CH$_2$)$_n$—X—[C$_3$H$_5$(OH)]—Y—(CH$_2$)$_m$— in which

C$_3$H$_5$(OH) is the structure:

—CH$_2$—CH—CH$_2$—   or   —CH—CH$_2$—   or
        |                              |
        OH                          CH$_2$OH

-continued

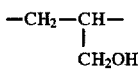

m and n, which are identical or different, are 0, 1, 2, 3 or 4;

X and Y are identical and are —O— or —S—;

or X is O and Y is S or X is S and Y is O, or A is

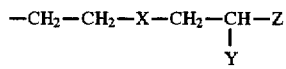

where

Y is OH, and

Z is

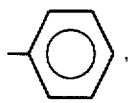

—CH$_3$, —CH$_2$OH, —CH$_2$OCOCH$_3$ or alternatively Y is —CH$_2$OH and Z is —O—COCH$_3$ X is —O—, —S—,

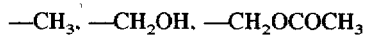

or A is:

—CH=CH—CH$_2$—O—CH$_2$—[C$_4$H$_4$—OW]

where

C$_2$H$_4$OW is

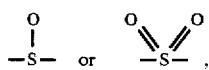

W is:

—OR, —SR, —COOR,

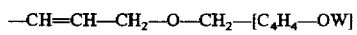

R is a linear or branched C$_1$-C$_{18}$ alkyl radical,

R' is —CH$_3$ or —OH, in the ortho or para position;

or A is a C$_n$F$_{2n+1}$—C$_2$H$_4$OH compound wherein n is 6 or 8 or A is a R CF$_2$—(OC$_2$F$_4$)$_p$—(OCF$_2$)$_q$—OCF$_2$R compound wherein p/q is from 0.5 to 1.5 and R is CH$_2$OH,

CH$_2$(OCH$_2$CH$_2$)$_t$OH where t is 1 or 2, or

CH$_2$OCH$_2$CHOHCH2OH, 0.1 to 99% by weight with respect to the total composition weight of at least one hydrocarbon glycol having two hydroxyl radicals, wherein no surfactant is present in said composition.

2. Composition according to claim 1 wherein the substitution ratio for the hydrogen atoms bonded to carbon by fluorine atoms for the fluorinated compounds is between 0.5 and 100%.

3. Composition according to claim 1 wherein the organofluorinated hydrocarbon compound has the following formula (II):

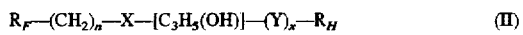

wherein

C$_3$H$_5$(OH) is the structure:

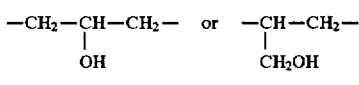

RH is a linear or branched C$_1$-C$_{22}$ alkyl radical or a mixture of linear or branched C$_1$-C$_{22}$ alkyl radicals or an aryl or aralkyl radical;

R$_F$ is a C$_4$-C$_{22}$ perfluoroalkyl radical;

n is between 0 and 4;

X is O, S,

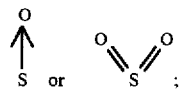

x is 0 or 1;

Y is O, S,

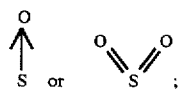

provided that when X is S,

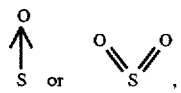

Y is not S,

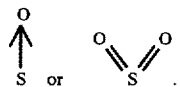

4. Composition according to claim 1 wherein the hydrocarbon glycol has a chain having 2 to 30 carbon atoms.

5. Composition according to claim 1 wherein the hydrocarbon glycol has 3 to 12 carbon atoms.

6. Composition according to claim 1 comprising at least one glycol comprising at least four carbon atoms and at least one organofluorinated hydrocarbon compound having the following formula (II):

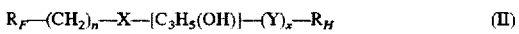

wherein $C_3H_5(OH)$ is the structure:

$$-CH_2-\underset{\underset{OH}{|}}{CH}-CH_2- \quad \text{or} \quad -CH-\underset{\underset{CH_2OH}{|}}{CH_2}-$$

(Ia)  (Ib)

$R_H$ is a linear or branched $C_1$–$C_{22}$ alkyl radical or a mixture of linear or branched $C_1$–$C_{22}$ alkyl radical or an aryl or aralkyl radical;

$R_F$ is a $C_4$–$C_{22}$ perfluoroalkyl radical;

n is between 0 and 4;

X is O, S, $$\overset{O}{\underset{S}{\uparrow}} \quad \text{or} \quad \overset{O\diagdown\!\!\diagup O}{\underset{S}{\phantom{.}}};$$

x is 0 or 1;

Y is O, S, $$\overset{O}{\underset{S}{\uparrow}} \quad \text{or} \quad \overset{O\diagdown\!\!\diagup O}{\underset{S}{\phantom{.}}};$$

provided that when X is $$\overset{O}{\underset{S}{\uparrow}} \quad \text{or} \quad \overset{O\diagdown\!\!\diagup O}{\underset{S}{\phantom{.}}},$$

Y is not $$\overset{O}{\underset{S}{\uparrow}} \quad \text{or} \quad \overset{O\diagdown\!\!\diagup O}{\underset{S}{\phantom{.}}},$$

or the following formula (I'):

$$R_F-(CH_2)_n-X-[C_3H_5(OH)]-Y-(CH_2)_m-R'_F \qquad (I')$$

in which $C_3H_5(OH)$ represents the structures:

$$-CH_2-\underset{\underset{OH}{|}}{CH}-CH_2- \quad \text{or} \quad -CH-\underset{\underset{CH_2OH}{|}}{CH_2}- \quad \text{or}$$

(Ia)  (Ib)

$$-CH_2-\underset{\underset{CH_2OH}{|}}{CH}-$$

(Ic)

$R_F$ and $R'_F$, which are identical or different, represent a linear or branched perfluorinated $C_4$–$C_{20}$ alkyl radical or a mixture of linear or branched perfluorinated $C_4$–$C_{20}$ alkyl radicals;

m and n, which are identical or different, represent 0, 1, 2, 3 or 4 and X is O and Y is S or X is S and Y is O.

7. Composition according to claim 1 further comprising oils, waxes, silicones, perfluorinated oils, gelling agents for oily media, gelling agents for aqueous media, water, polyols having at least three hydroxyl groups, monoalcohols, urea, lactic acid, salts, filters, vitamins, hormones, antioxidants, preservatives, dyes, perfumes, amino acids or powders.

8. Method of preparing a homogeneous cosmetic composition consisting essentially of:

0.1 to 99% by weight with respect to the total composition weight of at least one organofluorinated hydrocarbon compound or a perfluorinated carbon compound having the following formula (I):

$$(R_F)_x-(A)_y-(R_H)z \qquad (I)$$

wherein x is 1, 2 or 3, y is 0 or 1 z is 0, 1, 2 or 3 provided that y and z are not simultaneously 0 and that when z is 0 x is 2 or 3, the functional radicals OH, SH, $NH_2$ and NH may be on one or more of the radicals $R_F$, A and $R_H$ by insertion in the case of NH or terminal or pendent substitution in the case of OH, SH and/or $NH_2$; $R_F$ has at least two of said functional radicals when y and z are both 0, $R_F$ is an aliphatic or aromatic, saturated or unsaturated, fluorinated radical with a linear, branched or cyclic chain which may be functionalized and/or interrupted by oxygen or sulfur or nitrogen and/or substituted by hydrogen atoms or other halogen atoms provided that, for any two carbon atoms of the backbone, no more than one of these substituents other than fluorine is present, $R_H$ is an aliphatic or aromatic, saturated or unsaturated, hydrocarbon radical with a linear, branched or cyclic chain which may be functionalized and/or interrupted by one or more oxygen or sulfur atoms or by one or more nitrogen atoms, A is a di-, tri- or quadrivalent radical which is $$\diagdown\!\!\underset{\diagup}{\overset{\diagdown}{C}}\!\!\diagup, \quad \diagdown\!\!\underset{\diagup}{CH-}, \quad -\underset{\diagdown}{N}\!\!\diagup, \quad -CO-N\!\!\underset{\diagdown}{\diagup},$$

$$-SO_2N\!\!\underset{\diagdown}{\diagup}, \quad -O-\underset{\underset{O}{|}}{\overset{\overset{O}{\|}}{P}}-O-$$

or an unsaturated ethylene structure;

or A is $$-(CH_2)_n-X-[C_3H_5(OH)]-(Y')_x-$$

wherein $C_3H_5(OH)$ is the structure:

$$-CH_2-\underset{\underset{OH}{|}}{CH}-CH_2- \quad \text{or} \quad -CH-\underset{\underset{CH_2OH}{|}}{CH_2}-$$

(Ia)  (Ib)

n is between 0 and 4;

X is O, S,

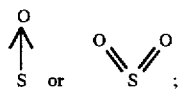

x is 0, or 1;
Y is O, S,

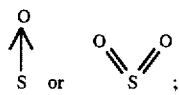

provided that when X is

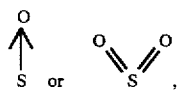

Y is not

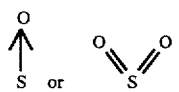

or A is

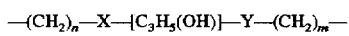

in which
$C_3H_5(OH)$ is the structure:

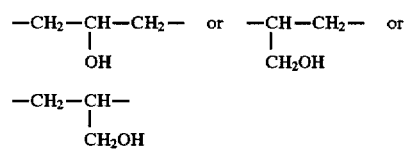

m and n, which are identical or different, are 0, 1, 2, 3 or 4;
X and Y are identical and are —O— or —S—;
or X is O and Y is S or X is S and Y is O,
or A is

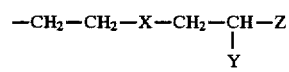

where
Y is OH, and
Z is

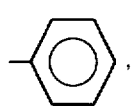

—CH$_3$, —CH$_2$OH, —CH$_2$OCOCH$_3$
or alternatively Y is —CH$_2$OH and Z is —O—COCH$_3$ X is —O—, —S—,

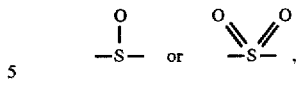

or A is:

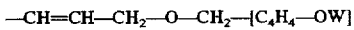

where
$C_2H_4OW$ is

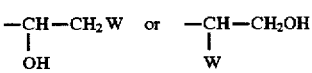

W is:

—OR, —SR, —COOR,

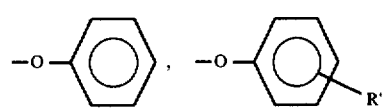

R is a linear or branched $C_1$–$C_{18}$ alkyl radical,
R' is —CH$_3$ or —OH, in the ortho or para position;
or A is a $C_nF_{2n+1}$—$C_2H_4OH$ compound
wherein
n is 6 or 8
or A is a R CF$_2$—(OC$_2$F$_4$)$_p$—(OCF$_2$)$_q$—OCF$_2$R compound
wherein
p/q is from 0.5 to 1.5
and R is CH$_2$OH,
CH$_2$(OCH$_2$CH$_2$)$_t$OH where t is 1 or 2, or
CH$_2$OCH$_2$CHOHCH$_2$OH, and
0.1 to 99% by weight with respect to the total composition weight of at least one hydrocarbon glycol having two hydroxyl radicals, in which method the constituents are mixed and brought to a miscibility temperature to produce a homogeneous phase, wherein no surfactant is present in said composition.

9. Composition according to claim 1 wherein the fluorinated compound has the following formula (III):

R CF$_2$—(OC$_2$F$_4$)$_p$—(OCF$_2$)$_q$—OCF$_2$R     (III)

wherein
p/q is from 0.5 to 1.5 and R is CH$_2$OH, CH$_2$(OCH$_2$CH$_2$)$_t$OH where t is 1 or 2, or CH$_2$OCH$_2$CHOHCH$_2$OH.

10. Composition according to claim 1, wherein the composition contains from 0.5 to 90% by weight with respect to the total composition weight of the fluorinated compound.

11. Composition according to claim 1, wherein the composition contains from 0.5 to 70% by weight with respect to the total composition weight of the glycol.

* * * * *